(12) United States Patent
Hopper

(10) Patent No.: US 10,753,932 B2
(45) Date of Patent: Aug. 25, 2020

(54) IMMUNOASSAY TEST APPARATUS

(71) Applicant: Axxin Pty Ltd, Fairfield, Victoria (AU)

(72) Inventor: William R. Hopper, East Ivanhoe (AU)

(73) Assignee: Axxin Pty Ltd, Fairfield, Victoria (AU)

( * ) Notice: Subject to any disclaimer, the term of this patent is extended or adjusted under 35 U.S.C. 154(b) by 203 days.

(21) Appl. No.: 15/508,884

(22) PCT Filed: Sep. 4, 2015

(86) PCT No.: PCT/AU2015/050523
§ 371 (c)(1),
(2) Date: Mar. 3, 2017

(87) PCT Pub. No.: WO2016/033657
PCT Pub. Date: Mar. 10, 2016

(65) Prior Publication Data
US 2017/0184586 A1 Jun. 29, 2017

(30) Foreign Application Priority Data
Sep. 5, 2014 (AU) .............................. 2014903548

(51) Int. Cl.
*G01N 33/543* (2006.01)
*G01N 33/558* (2006.01)
(Continued)

(52) U.S. Cl.
CPC .......... *G01N 33/558* (2013.01); *B01L 3/5023* (2013.01); *B01L 3/502761* (2013.01);
(Continued)

(58) Field of Classification Search
None
See application file for complete search history.

(56) References Cited

U.S. PATENT DOCUMENTS 6,846,638 B2    1/2005   Shipwash
2011/0275162 A1  11/2011  Xie et al.
(Continued)

FOREIGN PATENT DOCUMENTS

JP    2011-196825     10/2011
WO    WO2012/012499   1/2012
WO    WO2014/113770   7/2014

OTHER PUBLICATIONS

Supplementary European Search Report EP15838695, dated Jan. 26, 2018 6 pages.
(Continued)

*Primary Examiner* — Rebecca M Giere
(74) *Attorney, Agent, or Firm* — Fish & Richardson P.C.

(57) ABSTRACT

An immunoassay test apparatus, including:
  a label signal sensor that detects label signals emitted by at least one label conjugated to an antibody or antigen of an immunoassay test device such as a lateral flow test strip or microfluidic cartridge, and outputs sensor data representing the detected label signals;
  a label imaging component that processes the sensor data to generate label data representing spatial locations of the detected label signals;
  a test result image generator that processes the label data to generate test result image data representing a visual image of the spatial arrangement of the detected label signals; and
  a display component that displays the test result image to a user of the immunoassay test apparatus to enable the user to evaluate the result of the immunoassay test.

4 Claims, 7 Drawing Sheets

(51) Int. Cl.
  *G01N 21/84* (2006.01)
  *G01N 33/53* (2006.01)
  *B01L 3/00* (2006.01)
  *G01N 21/64* (2006.01)
  *G01R 33/12* (2006.01)
  *G06K 9/62* (2006.01)
  *G06T 11/60* (2006.01)

(52) U.S. Cl.
  CPC ..... *G01N 21/6428* (2013.01); *G01N 21/8483* (2013.01); *G01N 33/5302* (2013.01); *G01N 33/54366* (2013.01); *G01R 33/1269* (2013.01); *B01L 2300/0654* (2013.01); *G01N 2021/6439* (2013.01); *G06K 9/6267* (2013.01); *G06T 11/60* (2013.01)

(56) References Cited

U.S. PATENT DOCUMENTS

| | | |
|---|---|---|
| 2012/0300194 A1 | 11/2012 | Zimenkov et al. |
| 2013/0161190 A1 | 6/2013 | Ewart |
| 2013/0162981 A1 | 6/2013 | Emeric et al. |
| 2014/0065647 A1 | 3/2014 | Mamenta |
| 2014/0227681 A1* | 8/2014 | Fleming ............ G01N 21/6408 435/5 |

OTHER PUBLICATIONS

International Search Report and Written Opinion in International Application No. PCT/AU2015/050523, dated Nov. 10, 2015, 8 pages.

* cited by examiner

IMMUNOASSAY TEST APPARATUS

CROSS-REFERENCE TO RELATED APPLICATIONS

This application is a National Stage application under 35 U.S.C. § 371 of International Application No. PCT/AU2015/050523, filed Sep. 4, 2015, which claims the benefit of AU Application No. 2014903548, filed on Sep. 5, 2014. The disclosures of the prior applications are incorporated by reference in their entirety.

TECHNICAL FIELD

The present invention relates to the general fields of diagnostic and biomedical testing using fluorescent immunoassay or lateral flow test strips or other diagnostic or test detection, particularly relating to an immunoassay test instrument or apparatus suitable for use in medical diagnostics at the Point-of-Care (POC) and in Physician's Office Laboratories (POL).

BACKGROUND

As described in the Wikipedia[1] at http://en.wikipedia.org/wiki/Immunoassay:

[1] The Wikipedia text quoted herein is released under CC-BY-SA, see http://creativecommons.org/licenses/by-sa/3.0.

"An immunoassay test is a biochemical test that measures the concentration of a substance in a biological liquid, typically serum or urine, using the reaction of an antibody or antibodies to its antigen. The assay takes advantage of the specific binding of an antibody to its antigen. Monoclonal antibodies are often used as they only usually bind to one site of a particular molecule, and therefore provide a more specific and accurate test, which is less easily confused by the presence of other molecules. The antibodies picked must have a high affinity for the antigen (if there is antigen available, a very high proportion of it must bind to the antibody).

Both the presence of antigen or antibodies can be measured. For instance, when seeking to detect the presence of an infection the concentration of antibody specific to that particular pathogen is measured. For measuring hormones such as insulin, the insulin acts as the antigen.

For numerical results, the response of the fluid being measured must be compared to standards of a known concentration. This is usually done though the plotting of a standard curve on a graph, the position of the curve at response of the unknown is then examined, and so the quantity of the unknown found.

Detecting the quantity of antibody or antigen can be achieved by a variety of methods. One of the most common is to label either the antigen or antibody. The label may consist of an enzyme, enzyme immunoassay (EIA)), radioisotopes such as 1-125 Radioimmunoassay (RIA), magnetic labels (magnetic immunoassay—MIA) or fluorescence. Other techniques include agglutination, nephelometry, turbidimetry and Western Blot. A number of these do form a directly visible line or test output but require an instrument to measure or capture the test output.

Immunoassays can be divided into those that involve labelled reagents and those which involve non-labelled reagents. Those which involve labelled reagents are divided into homogenous and heterogeneous (which require an extra step to remove unbound antibody or antigen from the site, usually using a solid phase reagent) immunoassays. Heterogeneous immunoassays can be competitive or non-competitive.

In a competitive immunoassay, the antigen in the unknown sample competes with labelled antigen to bind with antibodies. The amount of labelled antigen bound to the antibody site is then measured. In this method, the response will be inversely proportional to the concentration of antigen in the unknown. This is because the greater the response, the less antigen in the unknown was available to compete with the labelled antigen.

In non-competitive immunoassays, also referred to as the "sandwich assay," antigen in the unknown is bound to the antibody site, and then labelled antibody is bound to the antigen. The amount of labelled antibody on the site is then measured. Unlike the competitive method, the results of the non-competitive method will be directly proportional to the concentration of the antigen. This is because labelled antibody will not bind if the antigen is not present in the unknown sample.

Because homogeneous assays do not require this step, they are typically faster and easier to perform."

As described in the Wikipedia[1] at http://en.wikipedia.org/wiki/Lateral flow test:

[1] The Wikipedia text quoted herein is released under CC-BY-SA, see http://creativecommons.org/licenses/by-sa/3.0.

"Lateral flow tests also known as Lateral Flow Immunochromatographic Assays are a simple device intended to detect the presence (or absence) of a target analyte in sample (matrix). Most commonly these tests are used for medical diagnostics either for home testing, point of care testing, or laboratory use. Often produced in a dipstick format, Lateral flow tests are a form of immunoassay in which the test sample flows along a solid substrate via capillary action. After the sample is applied to the test it encounters a coloured reagent which mixes with the sample and transits the substrate encountering lines or zones which have been pretreated with an antibody or antigen. Depending upon the analytes present in the sample the coloured reagent can become bound at the test line or zone. Lateral Flow Tests can operate as either competitive or sandwich assays.

In principle any coloured particle can be used, however most tests commonly use either latex (blue colour) or nanometre sized particles of gold (red colour). The gold particles are red in colour due to localized surface Plasmon resonance. Fluorescent or magnetic labelled particles can also be used—however these require the use of an electronic reader to access the test result.

The sample first encounters coloured particles which are labelled with antibodies raised to the target analyte. The test line will also contain antibodies to the same target, although it may bind to a different epitope on the analyte.

The test line will show as a coloured band in positive samples.

The sample first encounters coloured particles which are labelled with the target analyte or an analogue. The test line contains antibodies to the target/its analogue. Unlabelled analyte in the sample will block the binding sites on the antibodies preventing uptake of the coloured particles.

The test line will show as a coloured band in negative samples.

Most tests are intended to operate on a purely qualitative basis. However it is possible to measure the intensity of the test line to determine the quantity of analyte in the sample. Implementing a Magnetic immunoassay (MIA) in the lateral flow test form also allows for getting a quantified result.

While not strictly necessary, most tests will incorporate a second line which contains an antibody that picks up free latex/gold in order to confirm the test has operated correctly . . .

Time to obtain the test result is a key driver for these products. Tests can take as little as a few minutes to develop. Generally there is a trade-off between time and sensitivity—so more sensitive tests may take longer to develop. The other key advantage of this format of test compared to other immunoassays is the simplicity of the test—typically requiring little or no sample or reagent preparation . . .

Probably the most well known examples of lateral flow tests are home pregnancy tests. However rapid tests or point of care tests are available for a wide range of applications including: HIV tests, Troponin T, test Malaria tests, drugs of Abuse tests, Fertility tests, Respiratory disease tests etc. Clinical tests can be applied to urine, saliva, blood, or stool samples. Tests are available for both human and animal diagnostics. Tests are also available for non clinical applications including testing food and water for contaminants."

FIG. 1 shows a typical prior art lateral or capillary flow pad assembly or strip as commonly used in rapid diagnostic applications. The strip contains an absorptive sample application or input pad 102, a conjugate pad 104, a membrane 106 along which the analyte flows, and a waste adsorbing pad 108. These components are bonded by an adhesive layer 110, onto a carrier strip 112, usually constructed from plastic sheet.

Immobilised on the membrane (typically nitrocellulose) are one or several test regions or line(s) 114 containing capture antigens or antibodies for the target(s) of interest, and a control region or line 116 containing a control capture antigen or antibody. As described above, visible or colored or fluorescent labels are incorporated, such that the test result is displayed as one or more visible or otherwise optically detectible lines at the test region(s) 114 and/or the control region 116.

Lateral flow strips such as that shown in FIG. 1 are often contained in a plastic cassette having an opening for sample introduction and a open or transparent "window" for viewing the test and control lines 114, 116.

Currently, lateral flow and other similar types of biomedical test strips are widely used to diagnose a range of medical conditions from pregnancy, health markers and infectious diseases, for example flu.

An immunoassay test device such as a lateral flow test strip lateral flow test strip or microfluidic cartridge can be broadly classified into one of two categories or types, depending on whether the immunoassay test device result can be determined by direct visual inspection of the test strip by a human user, (e.g., by reflectance or absorption), without requiring any test instrument or stimulating (e.g., optical) signal to determine the results of the test. For example, the test result of a pregnancy test strip can be viewed in the home by simple visual inspection under natural or otherwise ordinary ambient lighting conditions. For convenience of description, this general type of immunoassay test device is referred to herein as a "traditional" immunoassay test device, irrespective of its physical form.

Conversely, some other types of immunoassay test device (including those where fluorescent or magnetic labels are used) produce a test result that cannot be seen by ordinary or direct visual inspection, often requiring a stimulating signal and/or an appropriate type of sensor to detect the presence of the test lines on the strip (for example an optical signal of a specific wavelength or wavelength range, or a magnetic stimulating signal in order to stimulate the emission of a second signal from the test strip that is indicative of the test result). Furthermore, in some instances (e.g., where the label is fluorescent), the emitted second signal may be an optical signal technically visible to the eye of a user, but in a format that it outside the experience of most users such that can not be readily interpreted by a typical or inexpert user. For example, a traditional lateral flow strip result is readily assessed by an inexpert user, because it is in the form of dark absorptive lines in a red or blue or black colour against a light or white background (the membrane). However, a test result viewed under stimulation as described above might be visible only as feint lines on a dark background.

Additionally, the stimulated output can typically only be effectively imaged or sensed after the stimulating signal has been separated, for example after passing through a bandpass filter and associated optical components, and usually in the absence of ambient lighting. In other cases, the emitted second signal may not be an optical signal at all, requiring an appropriate type of sensor to detect the emitted second signal and processing of the detected signal to determine the test result.

The present invention particularly relates to this second broad class or type of immunoassay test device, where the test result is not visible to a human observer, at least without the assistance of a test instrument or apparatus. In particular, the inventor has identified a difficulty with these types of lateral flow test strips in which the test result is not directly visible to a user by simply viewing the lateral flow test strip under natural or ambient lighting. These types of tests require the use of an electronic reader instrument and/or at least specialised illumination to assess the result of the test. Currently, these test instruments or apparatus analyse the second signal emitted from the test strip in order to automatically assess the (binary) result of the test, displaying the results as a simple binary test result (e.g., "pass" or "fail") or, at best, as a quantitative (numeric) value.

Although the lack of ambiguity in the test result provided by such an instrument may have direct application, the information that is available to the user is very limited. In particular, a simple binary test result does not provide any indication of the reliability of the assessment performed by the test instrument or apparatus, thus making it difficult for a user of the test instrument to have great confidence in the test result in the absence of any other information about the test result.

It is desired to address or alleviate one or more difficulties of the prior art, or at least to provide a useful alternative.

SUMMARY

In accordance with some embodiments of the present invention, there is provided an immunoassay test apparatus, including:
  a label signal sensor that detects label signals emitted by at least one label conjugated to an antibody or antigen of an immunoassay test device such as a lateral flow test strip or microfluidic cartridge, and outputs sensor data representing the detected label signals;

a label imaging component that processes the sensor data to generate label data representing spatial locations of the detected label signals;

a test result image generator that processes the label data to generate test result image data representing a visual image of the spatial arrangement of the detected label signals; and a display component that displays the test result image to a user of the immunoassay test apparatus to enable the user to evaluate the result of the immunoassay test.

The immunoassay test apparatus may further include a device imaging component that acquires or accesses device image data representing a visual image of at least a test result portion of the immunoassay test device from which the detected label signals were emitted; wherein the test result image generator processes the label data and the device image data to generate the test result image data, the test result image data representing a composite image of at least the test result portion of the immunoassay test device combined with features that visualise the spatial locations of the detected label signals from the test result portion of the immunoassay test device at corresponding locations of the composite image.

In accordance with some embodiments of the present invention, there is provided an immunoassay test apparatus, including:
    a label signal sensor that detects label signals emitted by at least one label conjugated to an antibody or antigen of an immunoassay test device such as a lateral flow test strip or microfluidic cartridge, and outputs sensor data representing the detected label signals;
    a label imaging component that processes the sensor data to generate label data representing spatial locations of the detected label signals;
    a device imaging component that acquires or accesses device image data representing a two-dimensional image of at least a test result portion of the immunoassay test device from which the detected label signals were emitted;
    a test result image generator that processes the label data and the device image data to generate test result image data representing a composite image of at least the test result portion of the immunoassay test device combined with features that visualise the spatial locations of the detected emissions from the test result portion of the immunoassay test device; and
    a display component that displays the composite image to a user of the immunoassay test apparatus to enable the user to evaluate the result of the immunoassay test.

In some embodiments, the at least one label includes a magnetic label, and the label signal sensor includes a magnetic sensor that detects magnetic fields emitted by the magnetic label.

In some embodiments, the at least one label includes a fluorescent label, and the label signal sensor includes an optical sensor that detects optical emissions from the fluorescent label.

In some embodiments, the immunoassay test apparatus includes a label stimulation transducer that emits a signal to cause the at least one label to emit the label signals.

In some embodiments, the immunoassay test device is a lateral flow test strip. In some embodiments, the immunoassay test device is a microfluidic cartridge.

In accordance with some embodiments of the present invention, there is provided an immunoassay test process, including:
    detecting label signals emitted by at least one label conjugated to an antibody or antigen of an immunoassay test device such as a lateral flow test strip or microfluidic cartridge to generate sensor data representing the detected label signals;
    processing the sensor data to generate label data representing spatial locations of the detected label signals;
    processing the label data to generate test result image data representing a visual image of the spatial arrangement of the detected label signals; and
    displaying the test result image to a user of the immunoassay test apparatus to enable the user to evaluate the result of the immunoassay test.

In some embodiments, the immunoassay test process further includes acquiring or accessing device image data representing a visual image of at least a test result portion of the immunoassay test device from which the detected label signals were emitted; wherein said step of processing the label data includes processing the label data and the device image data to generate the test result image data, the test result image data representing a composite image of at least the test result portion of the immunoassay test device combined with features that visualise the spatial locations of the detected label signals from the test result portion of the immunoassay test device at corresponding locations of the composite image.

In accordance with some embodiments of the present invention, there is provided an immunoassay test process, including:
    detecting label signals emitted by at least one label conjugated to an antibody or antigen of an immunoassay test device such as a lateral flow test strip or microfluidic cartridge to generate sensor data representing the detected label signals;
    processing the sensor data to generate label data representing spatial locations of the detected label signals;
    acquiring or accessing device image data representing a two-dimensional image of at least a test result portion of the immunoassay test device from which the detected label signals were emitted;
    processing the label data and the device image data to generate test result image data representing a composite image of at least the test result portion of the immunoassay test device combined with features that visualise the spatial locations of the detected emissions from the test result portion of the immunoassay test device; and
    displaying the composite image to a user of the immunoassay test apparatus to enable the user to evaluate the result of the immunoassay test.

In some embodiments, the at least one label includes a magnetic label, and the label signal sensor includes a magnetic sensor that detects magnetic fields emitted by the magnetic label.

In some embodiments, the at least one label includes a fluorescent label, and the label signal sensor includes an optical sensor that detects optical emissions from the fluorescent label.

In some embodiments, the immunoassay test process includes controlling a label stimulation transducer to emit a signal to cause the at least one label to emit the label signals.

In some embodiments, the immunoassay test device is a lateral flow test strip. In some embodiments, the immunoassay test device is a microfluidic cartridge.

BRIEF DESCRIPTION OF THE DRAWINGS

Some embodiments of the present invention are hereinafter described, by way of example only, with reference to the accompanying drawings, wherein.

DETAILED DESCRIPTION

Embodiments of the present invention address the prior art difficulties described above by using a sensor to detect the spatial arrangement of label signals representing the test result of an immunoassay test device such as a lateral flow test strip or microfluidic cartridge, and processing the output from the sensor to synthesise or otherwise generate an image of the test result that appears to a human observer as though it was a traditional immunoassay test result that can be readily viewed and assessed by visual inspection under natural or ambient light. For example, in the typical case of the immunoassay test device being a lateral flow test strip, the generated image represents the test result in the form of parallel test and control lines, typically (but not necessarily) as coloured lines on a white background. The image may represent the lines in isolation, or, more conveniently, superimposed onto an image of the immunoassay test device, which may be an acquired image of the actual immunoassay test device whose test result is displayed in the image.

Figure 1:
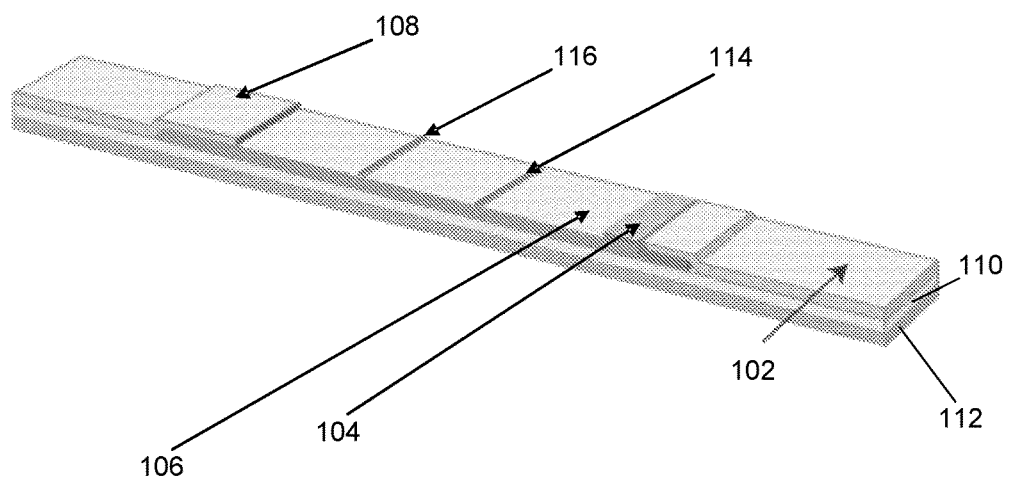
FIG. 1 is a schematic diagram of a prior art lateral flow test strip device.
Figure 2:
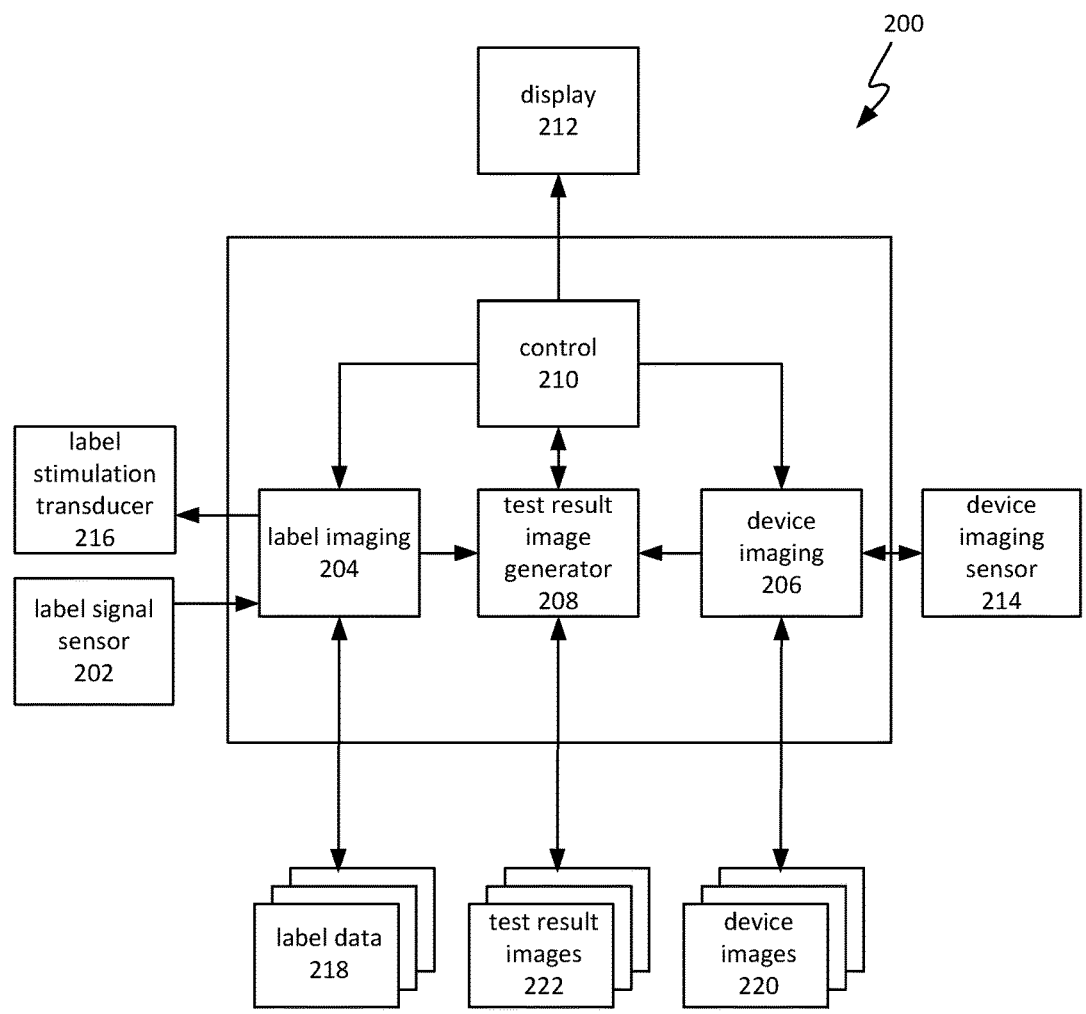
FIG. 2 is a block diagram showing the functional components of an embodiment of an immunoassay test instrument.

FIG. 2 is a block diagram showing the functional components of an immunoassay test instrument or apparatus 200 in accordance with an embodiment of the present invention. The instrument 200 includes a label signal sensor 202, a label imaging component 204, a device imaging component 206, a test result image generator 208, and a display 212. The operation and coordination of the functional components 202 to 208 is controlled by a control component 210 based on user input received from a user of the test instrument 200. In some embodiments, the test instrument 200 may also include a device imaging sensor 214 and/or a label stimulation transducer 216, although either or both of these components may be omitted in some embodiments, as described below.

Figure 3:
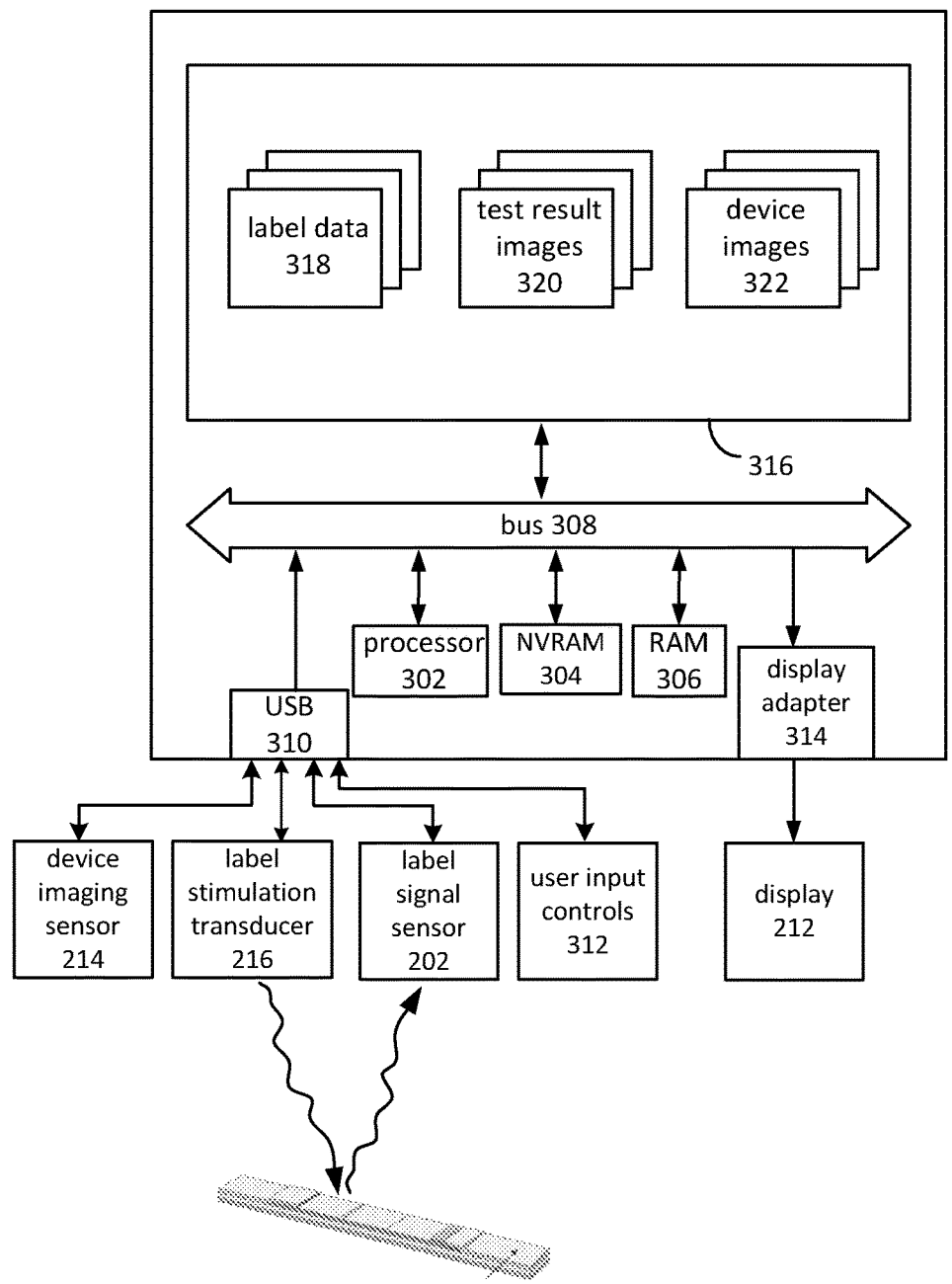
FIG. 3 is a block diagram showing hardware components of the immunoassay test instrument.

FIG. 3 is a block diagram showing the major hardware components of one embodiment of an immunoassay test instrument providing the components shown in FIG. 2. The instrument includes at least one processor 302, non-volatile memory 304, and random access memory (RAM) 306, all interconnected by a shared bus 308. In the described embodiment, the processor 302 is a microprocessor, the non-volatile memory 304 is flash memory, and the functional components 204 to 210 of FIG. 2 are stored in the form of firmware in the flash memory 304. When the instrument is initialised, the functional components 204 to 210 are loaded from the flash memory 304 into the test instrument's RAM 306 for execution by the processor 302.

In an alternative embodiment, the processor 302 is a field-programmable gate array (FPGA), and the functional components 204 to 210 are stored in the non-volatile memory 304 in the form of configuration data for the FPGA 302. However, it will be apparent to those skilled in the art that the immunoassay test instrument described herein may take various alternative forms, and the functions performed by the functional components 204 to 210 may be implemented in a variety of different ways apparent to those skilled in the art in light of this disclosure. For example, at least parts of the process 400 could alternatively be implemented as one or more dedicated hardware components, such as application-specific integrated circuits (ASICs), for example.

The immunoassay test instrument of FIG. 3 further includes one or more peripheral device interfaces 310, such as universal serial bus (USB) interfaces to interface the processor 302 to the label signal sensor 202 and (if present) the device imaging sensor 214 and the label stimulation transducer 216. The immunoassay test instrument also includes user input controls 312, which may be in the form of a keypad integrated into a housing of the instrument, a touchscreen component of the display 212, or an external input device such as a standard keyboard and mouse interfaced via a USB interface 310. Finally, a display adapter 314 is provided as an interface between the processor 302 and the display 212, which is typically in the form of an LCD screen or touchscreen, and which may be integrated into the housing of the test instrument. A non-volatile storage device 316 such as a magnetic or solid state drive or a compact flash (CF) device may be included to store the data acquired and/or generated by the immunoassay test instrument 200 using an immunoassay test process, as described below. Additionally, it will be apparent to those skilled in the art that in other embodiments the functional components 204 to 210 could be stored on the non-volatile storage device 316 rather than in the non-volatile memory 304.

Figure 4:
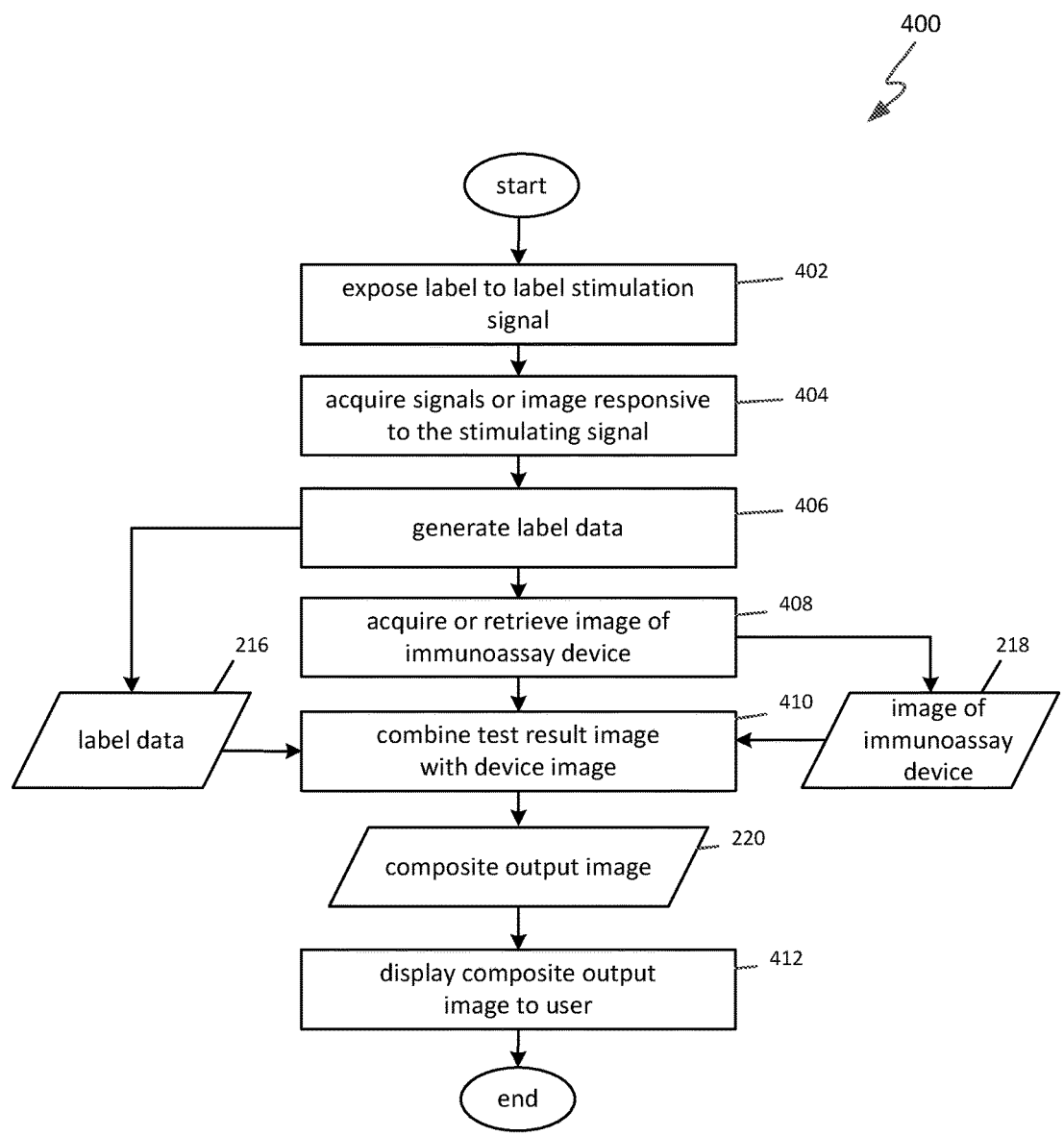
FIG. 4 is a flow diagram of an immunoassay test process executed by the immunoassay test instrument.

In some embodiments, the immunoassay test instrument 200 executes an immunoassay test process 400, as shown in the flow diagram of FIG. 4. The immunoassay test instrument 200 and process 400 address the difficulties of the prior art described above, as follows, with reference to FIGS. 2 and 4.

As described above, some forms of label conjugated to an antibody or antigen of an immunoassay test device require a stimulating signal in order to stimulate the labels so as to cause them to emit signals, referred to herein as "label signals", and thus allow their presence to be measured or otherwise detected. For example, fluorescent labels generally require illumination by a corresponding wavelength or range of wavelengths of invisible light in order to stimulate emission of light at a different wavelength or wavelengths (which may or may not be visible to the unassisted human eye). By contrast, labels in the form of magnetic beads do not require any form of stimulation, and all that is required is to detect their innate magnetic fields in order to measure or otherwise determine their presence at a given location.

In the case of an immunoassay test device including at least one label that requires a label stimulation signal in order for its presence to be measured, the immunoassay test instrument 200 includes the label stimulation transducer 216 (which may be, for example, an ultraviolet (UV) laser diode), and this is used to expose the corresponding label to the label stimulation signal at step 402 of the immunoassay test process 400. Conversely, in the case of an immunoassay test device that does not include any such label, the immunoassay test instrument 200 need not include the label stimulation transducer 216, and step 402 of the immunoassay test process 400 is omitted.

At step 404, the label signal sensor 202 detects the invisible (to the human eye) label signals emitted by the label. Where the label signals are optical signals, the label signal sensor 202 may be in the form of a standard photodiode or image sensor selected to have sufficient sensitivity in a corresponding wavelength range. For a typical fluorescent lateral flow test strip, this would involve imaging or measuring the membrane section of the strip to determine or capture the test and control line intensity distribution.

Conversely, where the label signals are in the form of magnetic signals (e.g., magnetic fields emitted by magnetic beads used as labels), the label signal sensor 202 is a magnetic sensor. It will be apparent to those skilled in the art that other forms of sensor may be used for other types of label signals.

Figure 5:
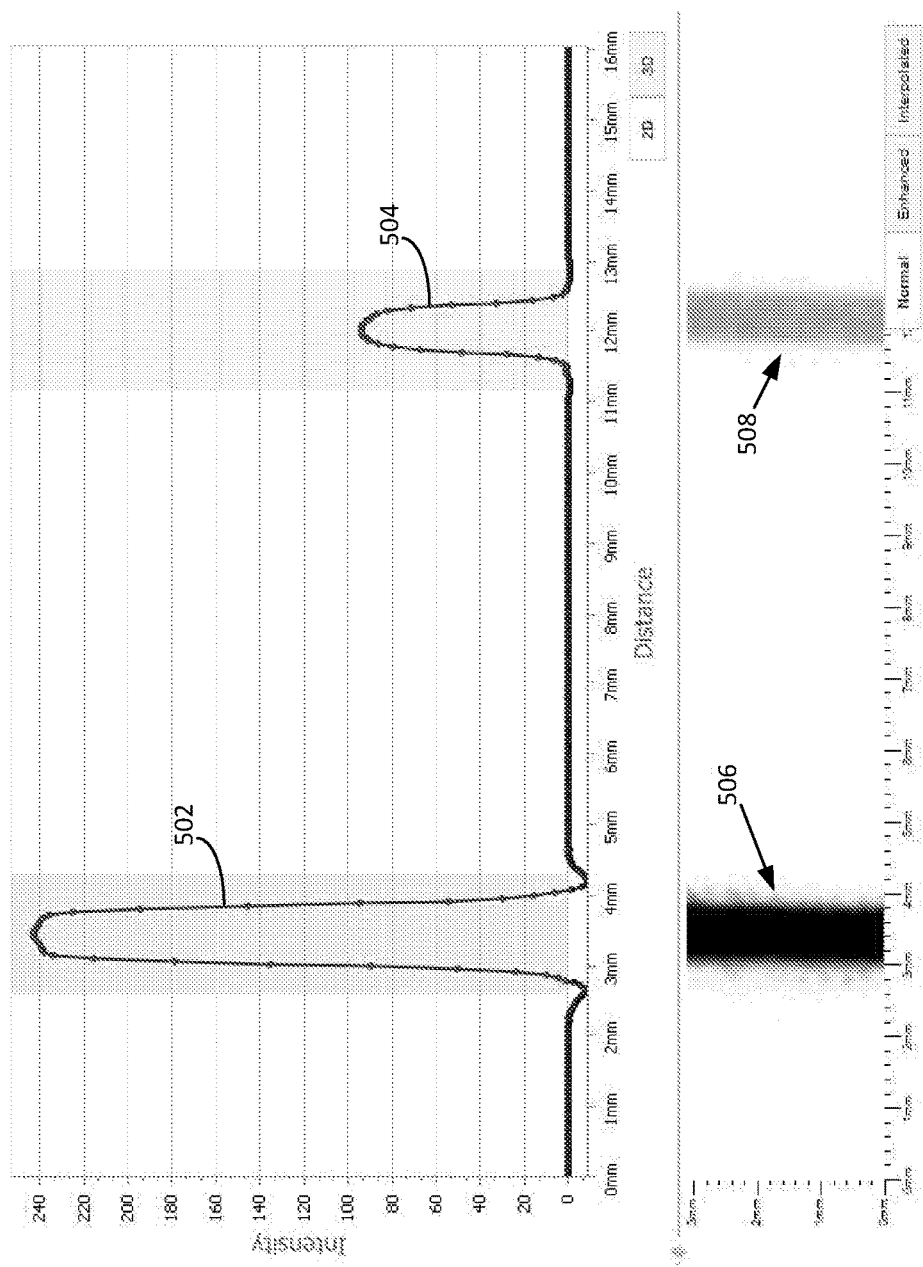
FIG. 5 is a graph of measured label signal intensity as a function of linear position along a lateral flow test strip.

At step 406, the output of the label signal sensor 202 is processed to generate label data 318 representing spatial locations of the detected label signals. In some embodiments, the label signal sensor 202 (e.g., an image sensor) acquires data in two spatial dimensions, and therefore can be considered to represent an image or spatial map of the detected label signals. Conversely, in some embodiments the sensor 202 itself (e.g., a photodiode or magnetic sensor) may not have a direct imaging capability, and the sensor 202 and/or the immunoassay test device are physically scanned in order to allow a two-dimensional image or spatial map to be generated by acquiring a set of separate measurements at successive relative spatial locations. In some embodiments, a one-dimensional relative scan data is acquired by relative movement of the sensor 202 and the immunoassay test device along one spatial direction. In the case of a lateral flow test strip, this would be along the longitudinal axis of the test strip in order to allow the separate lines to be spatially resolved. For example, FIG. 5 is a graph showing the measured intensity of the detected label signal as a function of spatial position along a lateral flow test strip, clearly showing the separate test and control lines 502, 504. This form of data is acquired by mounting the lateral flow test strip on a linear translation stage having a stepper motor or other form of actuator under control of the processor 302.

Thus the label data 220 may take any one of a variety of different possible forms, including an acquired two-dimensional image, or a set of (one or two-dimensional) spatial coordinates and associated values corresponding to the measured label signal intensities at those spatial coordinates.

At step 408, the device imaging component 206 acquires or otherwise accesses device image data 220 representing a two-dimensional image of at least the test result portion of the immunoassay test device. In some embodiments, the immunoassay test instrument 200 includes the device imaging sensor 214, which captures or acquires the device image data 220 in the form of a two-dimensional image of at least the test result portion of the actual immunoassay test device being used in the immunoassay test. Alternatively, the device imaging component 206 can retrieve the device image data 220 in the form of a previously stored image, which may be an image of a different immunoassay test device, preferably (but not necessarily) one having the same physical form as the actual immunoassay test device being used. As yet a further alternative, the device image data 220 may be retrieved in the form of a graphic (but non-photographic) representation of the immunoassay test device, such as a CAD drawing or other form of solid model, for example. It will be apparent that the position of step 408 relative to the preceding steps of the process 400 is entirely arbitrary, and for example this step could alternatively be, for example, the first step of the process 400 shown in FIG. 4.

At step 410, the test result image generator 208 processes the label data 218 and the device image data 220 to generate or synthesise a composite image 222. The composite image 222 is a composite image of at least the test result portion of the immunoassay test device, onto which are superimposed features visualising the two-dimensional spatial locations of the detected label signals. The composite image 222 is such that the composite image 222 visually represents the result of the immunoassay test as though the labels were traditional labels visible to the unassisted human eye.

Depending on the form of the label data 218, the test result image generator 208 may need to generate a synthesized test mark or lines that can then be graphically rendered as part of a visual representation of the immunoassay test device. For example, where the spatial information is acquired in only one dimension, such as the lateral flow test data shown in the upper part of FIG. 5, a two-dimensional representation of the corresponding test and control lines is generated by extending the measured line scans 502, 504 in a direction transverse to the scan direction to provide corresponding generally rectangular regions 506, 508, as shown in the lower part of FIG. 5.

Alternatively, where the label data 218 is in the form of a two-dimensional image of the label signals, the test result image generator 208 generally only needs to isolate the regions or pixels representing the two-dimensional spatial locations of the detected label signals and to superimpose them over the image of the device. It will be apparent that this can be done using any of a number of different standard image processing methods known to those skilled in the art, including for example cutting those regions or pixels from the label data 218 and pasting them (with appropriate scaling, rotation, and/or translation, if required) onto the device image, or using alpha compositing methods to make the other regions or pixels of the label data transparent, if required. Typically, it is also desirable to enhance the visual appearance of the pixels or regions of the detected label signals using standard image processing methods; for example, by appropriate colour mapping and/or gamma adjustments.

At step 412, the composite image 222 is then displayed on the display 212 of the immunoassay test instrument 200 to allow a user of the instrument 200 to evaluate the result of the immunoassay test.

Because the displayed composite image effectively visualises detected signals, and represents the test result as though it was a traditional immunoassay test device; i.e., one in which the labels are directly visible to the human eye under natural or otherwise ambient light, without requiring any test instrument or apparatus, the user can readily assess the reliability of the test result, and in most cases can have greater confidence in the test result than if the result is determined entirely by the test instrument and displayed only as a binary-valued test result (e.g., pass or fail) to the user.

In particular, the user can readily assess visual characteristics of the test result that are indicative of its reliability. For example, where the immunoassay test device is in the form of a lateral flow test strip, these visual characteristics include the degree to which the test lines have developed correctly, are in the correct position and format, and have the expected shape and edge definition. There are important safety and user confidence implications associated with these visual assessments, as a number of relatively subtle test errors and deficiencies can be easily recognized by a user who is familiar with the traditional display format. The high level of comfort that the composite image display thus provides to a user is of particular benefit where the test has important application, such as a diagnostic test used in care or treatment of patients, for example.

Typically, it is convenient to acquire a photographic image of the actual immunoassay test device being used at step 408, at least because the resulting image 218 can capture useful information specific to the device, including the particular markings on the consumable, such as printing, expiry date, barcode, 2D barcode, hand written notes, damage etc. This approach has additional utility because the image of the actual device is traceable and able to be utilized in audits, as evidence or for security purposes.

The resulting composite image 222 provides a test result that can be easily interpreted and accepted by the user to reinforce the binary result automatically calculated by the test instrument, such as positive or negative, displayed together with the composite image on the display 212 and, where appropriate, printed on a paper report or transmitted over a communications network such as the Internet (in embodiments where the immunoassay test instrument of FIG. 3 includes a network interface connector (NIC) connecting the instrument to a local or wide area network).

Alternatively, where the device image data 220 is in the form of a previously stored image, this image may be selected from a set of stored images 220 of several different types of consumable immunoassay test devices that can be used with the test instrument. In this case, the instrument selects the appropriate stored image from the set of images based on manual entry or selection by the user, or device type identification information determined using a barcode, RFID tag, or other form of identification of the actual immunoassay test device (as read by a barcode, RFID or other form reader device (not shown) connected to or integrated with the test instrument.

EXAMPLE I

Figure 6:
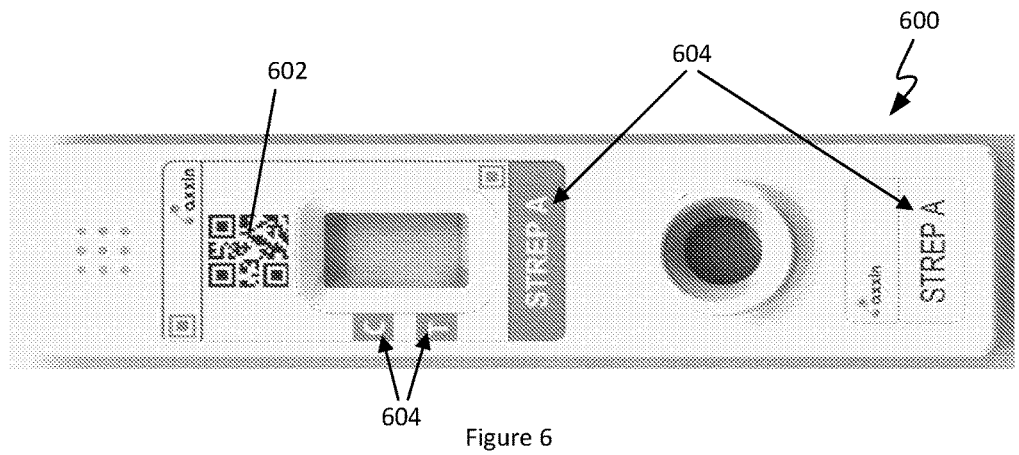
FIG. 6 is an image of a lateral flow test strip device captured by the immunoassay test instrument.

FIG. 6 is an image 600 of a consumable lateral flow test device, captured by an immunoassay test instrument as described above. Such an image 600 allows the instrument to determine: (i) the cartridge type, (ii) that the cartridge is undamaged and loaded correctly into the instrument, (iii) (by decoding the barcode 602 and identifying characters 604 on the cartridge label) the test type, lot number, calibration values to apply and expiry date.

Figure 7:
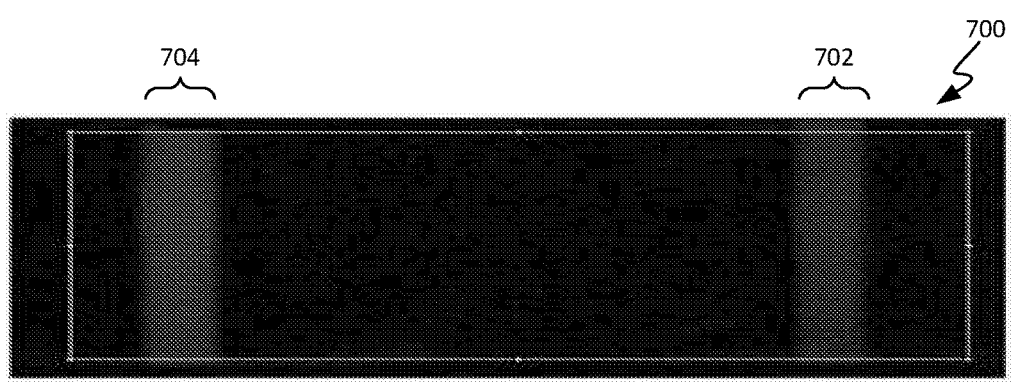
FIG. 7 is an image of test and control lines corresponding to the detected label signals emitted by fluorescent labels of the lateral flow test strip, as captured by the immunoassay test instrument.

The instrument is then switched to a florescence image capture mode to capture a fluorescence image 700 of the detection target and control lines 702, 704, as shown in FIG. 7. In this example, Europium fluorescence that has a red emission is used as the label. All of the background without emission appears black.

Figure 8:
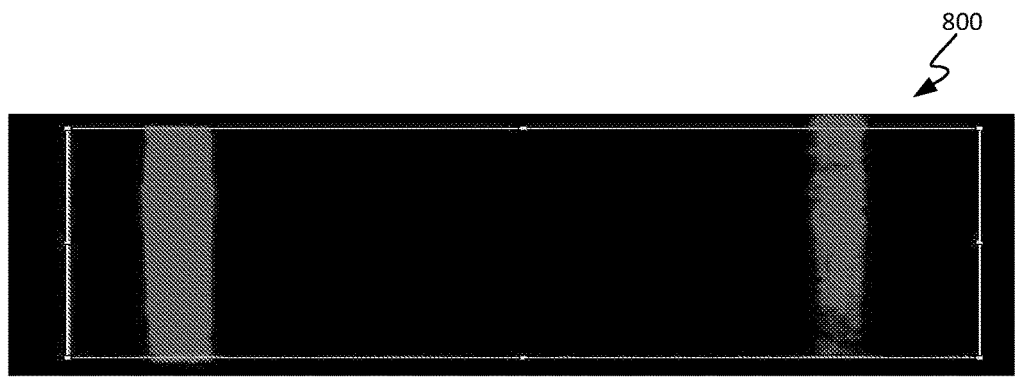
FIG. 8 is an image derived from the image of FIG. 7, following gamma adjustment to enhance the visual appearance of the test and control lines.

The captured image 700 is then subjected to standard software image enhancement to enhance the two red fluorescence marker regions 702, 704, in this example by adjusting the gamma of the image, resulting in the enhanced image 800 shown in FIG. 8.

Figure 9:
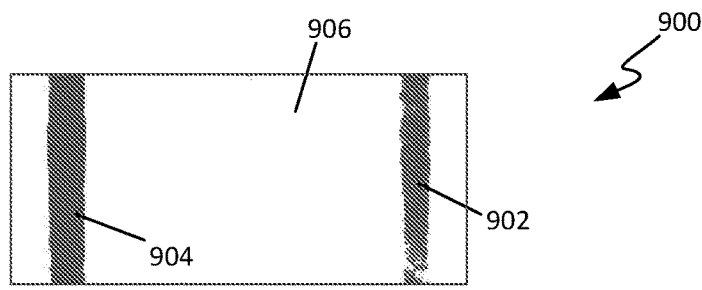
FIG. 9 is an image derived from the enhanced image of FIG. 8, showing the test and control lines isolated from the image background.

In this specific example, the enhanced image 800 was then converted to a colour inverse or negative. This has the advantage that the black background is converted to white, assisting with combining this image section with a largely white visual image of the test consumable. In this step the red test lines are converted to an inverse that is blue. The resulting image can then be used directly or further adjusted for display. In this example, the software image processing is further applied to change the colour and hue to convert the lines back to a red colour, as this is the preferred display colour for this type of test. The result is the image 900 shown in FIG. 9, consisting of mutually spaced red test 902 and control 902 lines on a white background 906.

As an alternative to the above, the enhanced image 800 can be converted to a monochrome image, in which the lines appear as light lines on a dark or black strip background. An inverse of the monochrome image then appears as black lines on a white strip that a user can readily understand and interpret.

Figure 10:
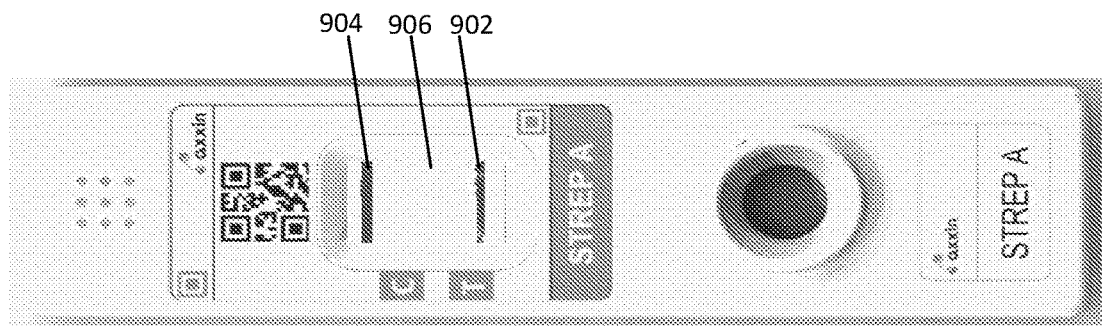
FIG. 10 is the composite image generated by the immunoassay test instrument by superimposing the isolated test and control lines of FIG. 11 on the lateral flow test strip image of FIG. 6.

In any case, the test result lines 902, 904 are then extracted (if required) or otherwise cropped, and then resized and overlaid and positioned over the image 600 of the lateral flow test strip device to form the composite image shown in FIG. 10. It will be apparent that the composite image represents the test result as though it was a traditional lateral flow test result visible to the unassisted human eye, with clear red lines 902, 904 on a white background 906, and within the test result region of the lateral flow test strip device. For example, the irregular edges of the test line 902 are clearly visible. Such features would not be apparent when fluorescent labels are used in prior art test instruments, which provide the test result in the form of a positive or negative binary result, with no opportunity to visually inspect the actual morphology or physical form of the control 904 and test 902 lines.

EXAMPLE II

Figure 11:
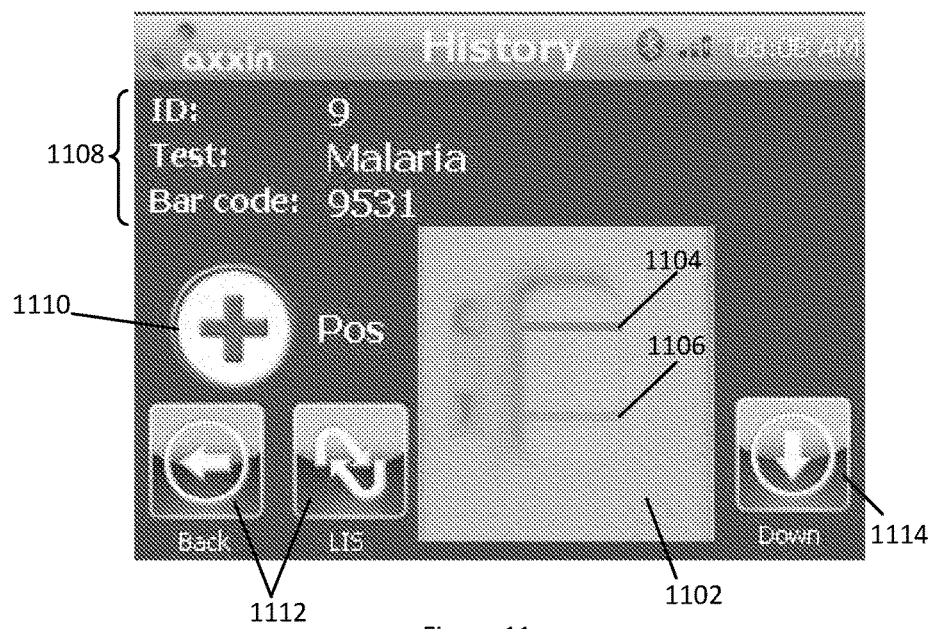
FIG. 11 is a screenshot taken from a portable immunoassay test instrument, showing a composite image of a lateral flow malaria test result, together with associated information on the test, automatically calculated test result, and user input controls.

FIG. 11 shows a screenshot of an interactive graphical user interface displayed on the LCD panel display of a portable immunoassay test instrument. The screenshot includes a composite test result image 1102 representing the test result region of a lateral flow strip for testing for the presence of influenza, where the actual control 1104 and test result 1106 lines were captured in a fluorescence image, extracted from the captured image, processed to allow the strip area to be displayed with colours and contrast analogous to a traditional lateral flow test strip, and superimposed on a captured image of the test result region of the actual test strip that was used in the test.

The screenshot also shows additional information 1108, 1110 on the test, including the test type and test result determined by automated analysis of the fluorescence image. The automated analysis is performed by measuring the intensities at the predetermined locations of the control line 1104 and test line 1106 on the strip. If both the control line 1104 and the test line 1106 are present above a predetermined intensity threshold, then the test result is deemed Positive, as represented by a positive test result icon 1110 and the accompanying text "Pos". User input controls 1112, 1114 are also shown, allowing the user to control the operation of the instrument.

In some test strips, more than two lines may be present. For example in the case of a Flu A/Flu B test, there will be three lines, Control, a Flu A test line and a Flu B test line.

Many modifications will be apparent to those skilled in the art without departing from the scope of the present invention.

The invention claimed is:

1. An immunoassay test apparatus comprising an immunoassay test device, wherein said immunoassay test device comprises a lateral flow test strip or microfluidic cartridge, said immunoassay test apparatus including:
 a processor and a memory, wherein said memory comprises:
 a label signal sensor that detects label signals emitted by at least one label conjugated to an antibody or antigen of said immunoassay test device and outputs sensor data representing the detected label signals;
 a label imaging component that acquires the sensor data and generates label data representing spatial locations of the detected label signals;
 a test result image generator that synthesizes a composite image comprising device image data representing a two-dimensional image of at least a test result portion of the immunoassay test device from which the detected label signals were emitted onto which the label data is superimposed to visualise the test result; and
 wherein said apparatus further includes a display component that displays the composite image to a user of the immunoassay test apparatus to enable the user to evaluate the result of the immunoassay test.

2. The immunoassay test apparatus of claim 1, wherein the at least one label includes a magnetic label, and the label signal sensor includes a magnetic sensor that detects magnetic fields emitted by the magnetic label.

3. The immunoassay test apparatus of claim 1, wherein the at least one label includes a fluorescent label, and the label signal sensor includes an optical sensor that detects optical emissions from the fluorescent label.

4. The immunoassay test apparatus of claim 1, including a label stimulation transducer that emits a signal to cause the at least one label to emit the label signals.

* * * * *